(12) United States Patent
Blaschke et al.

(10) Patent No.: US 10,183,234 B2
(45) Date of Patent: Jan. 22, 2019

(54) CROSSFLOW TRAY FOR A MASS TRANSFER COLUMN, MASS TRANSFER COLUMN AND USE OF THE MASS TRANSFER COLUMN

(71) Applicant: BASF SE, Ludwigshafen am Rhein (DE)

(72) Inventors: Tim Blaschke, Stuttgart (DE); Ulrich Cremer, Ludwigshafen (DE); Ulrich Hammon, Mannheim (DE)

(73) Assignee: BASF SE, Ludwigshafen am Rhein (DE)

( * ) Notice: Subject to any disclaimer, the term of this patent is extended or adjusted under 35 U.S.C. 154(b) by 199 days.

(21) Appl. No.: 15/072,463

(22) Filed: Mar. 17, 2016

(65) Prior Publication Data
US 2016/0271516 A1 Sep. 22, 2016

(30) Foreign Application Priority Data
Mar. 18, 2015 (DE) .................. 10 2015 204 904

(51) Int. Cl.
*B01D 3/32* (2006.01)
*B01D 3/20* (2006.01)
(Continued)

(52) U.S. Cl.
CPC ............ *B01D 3/324* (2013.01); *B01D 3/20* (2013.01); *B01D 3/225* (2013.01); *B01D 3/26* (2013.01);
(Continued)

(58) Field of Classification Search
CPC . B01D 3/16; B01D 3/20; B01D 3/225; B01D 3/26; B01D 3/324; B01F 3/04468;
(Continued)

(56) References Cited

U.S. PATENT DOCUMENTS 1,738,036 A * 12/1929 Chillas, Jr. ............... B01D 3/18
261/114.1
1,782,735 A * 11/1930 MacKenzie ............. B01D 3/22
202/158
(Continued)

FOREIGN PATENT DOCUMENTS

DE 27 18 858 A1 11/1978
DE 102 57 915 A1 10/2003
(Continued)

OTHER PUBLICATIONS

International Search Report and Written Opinion of the International Searching Authority dated Jun. 17, 2016 in PCT/EP2016/055637 filed Mar. 16, 2016 (with English translation of International Search Report only).

*Primary Examiner* — Renee Robinson
*Assistant Examiner* — Gabriel E Gitman
(74) *Attorney, Agent, or Firm* — Oblon, McClelland, Maier & Neustadt, L.L.P.

(57) ABSTRACT

The invention relates to a crossflow tray for a mass transfer column (27) in which a gas is conducted in countercurrent to a liquid, the crossflow tray (1) having passage orifices (3) for the gas and at least two downcomers (5), the downcomers (5) projecting beyond the top surface of the crossflow tray (1) and a collecting cup (13) being disposed beneath each downcomer (5). The downcomer (5) projects into the collecting cup (13), the minimum horizontal cross-sectional area of the collecting cup (13) is 1.2 to 4 times greater than the horizontal cross-sectional area of the downcomer (5) at the outlet, and the collecting cup (13) has a circumferential wall (15) having an overflow (19).
The invention further relates to a mass transfer column comprising the crossflow trays and to a use of the mass transfer column.

13 Claims, 4 Drawing Sheets

Figure 1:
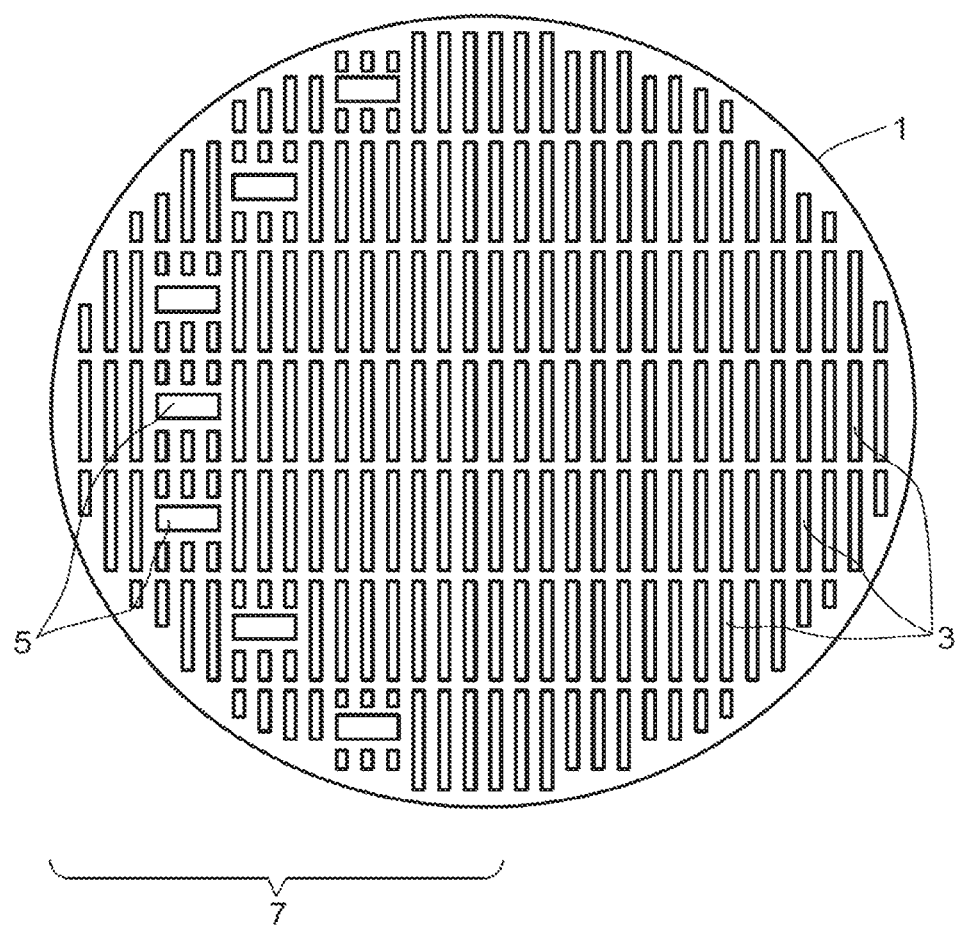

(51) Int. Cl.
  *B01D 3/22* (2006.01)
  *B01D 3/26* (2006.01)
  *B01F 3/04* (2006.01)
  *C07C 45/78* (2006.01)
  *C07C 51/42* (2006.01)
  *C07C 67/48* (2006.01)
  *B01J 19/00* (2006.01)
  *B01L 3/16* (2006.01)

(52) U.S. Cl.
  CPC ...... *B01F 3/04468* (2013.01); *B01F 3/04496* (2013.01); *C07C 45/783* (2013.01); *C07C 51/42* (2013.01); *C07C 67/48* (2013.01); *B01J 19/0006* (2013.01); *B01L 3/16* (2013.01)

(58) Field of Classification Search
  CPC .............. B01F 3/04496; B01J 19/0006; C07C 45/783; C07C 51/42; C07C 67/48
  See application file for complete search history.

(56) References Cited

U.S. PATENT DOCUMENTS

| | | | | |
|---|---|---|---|---|
| 2,206,507 A | * | 7/1940 | Kuhni | B01D 19/02 202/176 |
| 2,767,966 A | | 10/1956 | Chave | |
| 4,179,487 A | * | 12/1979 | Chekhov | B01J 19/305 202/158 |
| 4,273,618 A | | 6/1981 | Strang, Sr. | |
| 5,972,171 A | * | 10/1999 | Ross | B01D 45/14 202/158 |
| 6,123,323 A | * | 9/2000 | Yoneda | B01D 3/16 261/113 |
| 6,224,043 B1 | * | 5/2001 | Fan | B01D 3/20 261/114.1 |
| 6,371,454 B1 | * | 4/2002 | Gerla | B01D 3/20 261/114.1 |
| 2013/0274519 A1 | * | 10/2013 | Mueller-Engel | B01D 3/225 562/600 |
| 2015/0158011 A1 | | 6/2015 | Mueller-Engel et al. | |

FOREIGN PATENT DOCUMENTS

| | | |
|---|---|---|
| DE | 103 32 758 A1 | 5/2004 |
| DE | 10 2012 204 436 A1 | 10/2012 |
| GB | 2 002 650 A | 2/1979 |
| WO | WO 2013/139590 A1 | 9/2013 |

* cited by examiner

CROSSFLOW TRAY FOR A MASS TRANSFER COLUMN, MASS TRANSFER COLUMN AND USE OF THE MASS TRANSFER COLUMN

The invention relates to a crossflow tray for a mass transfer column in which a gas is conducted in countercurrent to a liquid, the tray having passage orifices for the gas and at least two downcomers, the downcomers projecting beyond the top surface of the crossflow tray and a collecting cup being disposed beneath each downcomer. The invention further relates to a mass transfer column comprising the crossflow tray and to a use of the mass transfer column.

Crossflow trays of this kind find use, for example, in the preparation of (meth)acrylic monomers. These comprise especially acrylic acid, methacrylic acid, acrolein, methacrolein, and esters of acrylic acid and esters of methacrylic acid.

(Meth)acrylic monomers are important starting compounds for preparation of polymers which find use, for example, as adhesives or as water-superabsorbent materials in hygiene articles.

Crossflow trays have passage orifices for the gas, the dimensions of which are such that no liquid runs off the tray through the passage orifices because of the gas flow. Additionally included are downcomers through which the liquid can run off. In a column, superposed crossflow trays are each rotated by 180° with respect to one another, such that liquid running off through downcomers in the upper tray hits the tray beneath on the side remote from the downcomers, flows over the tray to the downcomers in the tray and runs off through the downcomers. At the same time, the ascending gas flows through the liquid running transverse to the gas flow over the tray, which achieves intensive exchange between gas and liquid.

A corresponding mass transfer column having crossflow trays which is used for preparation of (meth)acrylic monomers is described, for example, in WO-A 2013/139590. In this case, collecting cups are disposed beneath each of the downcomers in order to obtain a static liquid seal of the downcomer. The liquid seal prevents gas from ascending through the downcomer. Since there is no liquid above the downcomer, the resistance offered to the gas is lower in the region of the downcomer, such that the gas rises preferentially through the downcomer, which worsens the exchange between gas and liquid. The height of the liquid level on the tray can be adjusted via liquid weirs on the downcomer. Only when the height of the liquid weir is reached can liquid run off from the tray through the downcomer.

GB-A 2 002 650 discloses trays for a mass transfer column, these having a plurality of downcomers, each of which has been provided with a weir for adjustment of the liquid level on the tray. The downcomers of the individual trays are arranged one on top of another and, in order that the liquid running off from the downcomer does not flow directly into the downcomer beneath, there is a deflecting plate below the outflow orifice of the downcomer, with which liquid running off is deflected into the region between two outflow orifices of the lower tray. However, what is achieved here is merely a deflection; no liquid seal of the downcomer can be achieved.

DE-A 27 18 858 describes a column having trays, each of which has a downcomer, with successive trays each rotated by 180° with respect to one another. The rotated arrangement of the trays creates a crossflow on the tray. For the passage of gas, orifices are provided, which are sealed beneath the downcomer of the upper tray with a cover plate, in order that the liquid running off does not flow off directly through the gas passage orifices of the tray.

Sieve trays each having lower-lying regions from which the liquid runs off onto the tray beneath, and higher-lying regions having orifices through which the ascending gas flows are known from U.S. Pat. No. 2,767,966. The trays are each arranged one on top of another such that the lower-lying regions of the upper tray are positioned above the higher-lying regions of the lower tray.

U.S. Pat. No. 4,273,618 discloses trays each having a downcomer and a collector. The trays are arranged in a column such that one downcomer ends above each collector, such that the liquid that runs off through the downcomer at first flows into the collector and, as soon as the liquid level reaches the height of the weir surrounding the collector, the liquid flows out of the collector onto the tray.

In none of the trays disclosed in GB-A 2 002 650, DE-A 27 18 858, U.S. Pat. Nos. 2,767,966 and 4,274,618 is a liquid seal possible, by which a bypass flow of the gas through the downcomers can be prevented.

Especially in the case of use of crossflow trays in mass transfer columns which are used in the preparation of (meth)acrylic monomers, there may be unwanted polymerization which cannot be suppressed even by polymerization inhibitors. Especially in the case of prolonged operating times, there is increased formation of unwanted polymer. This is especially disadvantageous because the operation of the mass transfer column has to be stopped regularly in order to remove the polymer formed, which can completely or partly occlude the gas passage orifices of the tray.

It is therefore an object of the present invention to provide a crossflow tray which can be used in a mass transfer column and which, when used, can remedy or at least reduce the disadvantages known from the prior art. It is a further object of the invention to provide a mass transfer column which can be operated over a prolonged period without formation of unwanted deposits.

This object is achieved by a crossflow tray for a mass transfer column in which a gas is conducted in countercurrent to a liquid, the tray having passage orifices for the gas and at least two downcomers, the downcomers projecting beyond the top surface of the crossflow tray and a collecting cup being disposed beneath each downcomer, wherein the downcomer projects into the collecting cup, the minimum horizontal cross-sectional area of the collecting cup being 1.2 to 4 times greater than the horizontal cross-sectional area of the downcomer at the outlet, and wherein the collecting cup has a circumferential wall having an overflow.

It has been found that, surprisingly, in the case of a tray configuration such that a collecting cup is disposed beneath each downcomer, the downcomer projects into the collecting cup and the collecting cup has a circumferential wall having an overflow, the formation of deposits can be reduced. Especially when the trays are used in a column which is used in the preparation of (meth)acrylic monomers, the formation of unwanted polymer can be reduced or prevented.

The use of the collecting cup into which the downcomer projects achieves a liquid seal which prevents bypass flow of the gas through the downcomer. The downcomer which projects into the collecting cup has the function of a siphon. In order to assure the working of the siphon, the collecting cup is configured in such a way that the wall of the collecting cup having the overflow is also configured in such a way that the liquid level in the collecting cup is sufficiently high that the downcomer dips into the liquid before liquid can flow out of the collecting cup via the overflow.

The passage orifices for the gas may have any desired geometry known to those skilled in the art which is suitable for passage orifices in crossflow trays. For example, the passage orifices may take the form, for example, of holes having any desired shape. Preferably, the passage orifices in this case are rectangular with the long edge at right angles to the main flow direction of the liquid on the tray, and the tray takes the form of a sieve tray having downcomers. As well as a rectangular configuration, any other shape is of course also conceivable for example in the form of a curved slot, an oval or a circle. The passage orifices may be disposed on the tray either in ordered form, for example in parallel or axial rows, or else in unordered form. In the case of curved slots, the passage orifices are preferably arranged concentrically about the center of the tray.

As an alternative to simple holes as passage orifices for the gas, it is also possible to configure the passage orifices as valves or as chimneys having a hood. In the case of valves, each passage orifice has a valve lid which is raised by the gas flowing through. This prevents liquid from the tray from running off through the valves when gas flow is too low. When the passage orifices are provided with a chimney having a hood, the configuration of the passage orifices corresponds to those as used on bubble-cap trays or tunnel-cap trays. The hood surrounds the chimney in such a way that gas flowing through the passage orifices is deflected into the liquid on the tray.

It is particularly preferable to use bubble-cap trays of the Thormann® type, in which the passage orifices take the form of rectangular bubble caps with deflecting plates for the gas.

In a preferred embodiment of the invention, the overflow is disposed on the side of the collecting cup facing away from the shell of the mass transfer column. This has the advantage that a relatively low liquid level is established in the region between the shell and runoff cup, which additionally has the result that greater entrainment of liquid is created, which keeps the regions above wet. Since no polymer forms at liquid-wetted sites, this can reduce or even prevent the formation of deposits. The term "spray shadow" is also used hereinafter to refer to the region which is not wetted by liquid entrained with the gas flow in the form of droplets.

It is particularly preferable when all the overflows are aligned such that the center axis of each overflow is aligned at right angles to the center axis of the tray. The side of the collecting cup facing away from the shell of the mass transfer column, irrespective of the cross-sectional shape of the collecting cup, is the region which points in the direction of the center axis of the tray. Irrespective of the width of the overflow, this means that the middle of the overflow points in the direction of the center axis of the tray. The center axis of the tray is a diameter line which is aligned such that the center axis that runs parallel to the surface of the tray for the overflow furthest removed from the center axis of the tray runs at right angles to the center axis of the tray. It is particularly preferable here when all the downcomers and hence all the overflows are arranged on one side of the center axis of the tray. Preferably, the overflows are aligned such that the center axes of all the overflows run parallel to one another. The center axis of an overflow is understood to mean the line running parallel to the surface of the tray which runs through the middle of the overflow and is typically a line of symmetry of the upper edge of the collecting cup that forms the overflow.

In the case of a configuration of the downcomers in the form of elongated holes which each run parallel, such that the downcomers and the collecting cups likewise have an elongated cross-sectional shape, it is advantageous when the overflows are arranged such that each is aligned in the direction of the center axis of the tray.

In the case of a rectangular or square cross-sectional shape of the collecting cup, it is particularly preferable for a wall of the square or rectangle to form the overflow. In the case of an oval cross-sectional shape with straight sides running parallel and curved sides which connect the straight sides, one of the curved sides preferably forms the overflow.

If the collecting cup has a circular cross-sectional shape, up to 80% of the wall of the circular collecting cup may form the overflow. Preferably not more than 50% of the wall of the circular collecting cup forms the overflow, and more preferably not more than 30%. The alignment of the overflow is preferably chosen such that, as already explained above, the center of the overflow points in the direction of the center of the tray.

The "cross-sectional shape" of the collecting cup is understood in the context of the present invention to mean the cross-sectional shape in a horizontal section through the collecting cup. As a result, the cross-sectional shape generally also corresponds to the shape of the collecting cup apparent from the top view of the collecting cup. In the case of non-vertical walls of the collecting cup, however, the cross-sectional shape may change from the base of the collecting cup to the upper edge of the walls. In general, however, in this case too, the cross-sectional shape will remain the same and only the size of the cross-sectional area will change.

The overflow through which the liquid runs out of the collecting cup may assume any desired form known to those skilled in the art which is possible for realization of an overflow. For example, it is possible to provide orifices in the wall of the collecting cup which act as overflow. However, it is preferable when the circumferential wall of the collecting cup forms the overflow by having a lower height in the region of the overflow. The height of the overflow is preferably chosen such that the wall in the region of the overflow is sufficiently high that the lower end of the downcomer is below the upper edge of the run off cup over its entire circumference.

In one embodiment of the invention, the circumferential wall runs at right angles to the base of the collecting cup. This has the advantage that the collecting cup, even at its upper end, does not constrict the cross section through which the gas flows any further than at the base. The gas flow is thus not accelerated any further between the base of the collecting cup and its upper end. This has the advantage that no liquid flowing out of the downcomer is entrained with the gas flow; in addition, the region which is wetted with liquid which is sprayed on by the gas flowing through the tray is also not reduced any further in size, such that a maximum region is wetted with liquid, such that the formation of polymer and hence the development of deposits is prevented.

If the walls of the collecting cups are inclined, the cross-sectional area of the collecting cup increases from the base in the direction of the upper edge of the walls of the collecting cup. The angle by which the walls are inclined with respect to the vertical is preferably less than 45°, more preferably less than 30° and especially less than 10°. However, it is most preferable when the walls of the collecting cup run parallel to the vertical, such that the angle is 0°.

The cross-sectional shape of the collecting cup, in one embodiment, corresponds to the cross-sectional shape of the collecting shaft. In one version of the invention, the collecting cup is disposed centrally beneath the collecting shaft, such that the distance of the wall of the downcomer in the region of the outflow orifice from the wall of the downcomer is equal at every point. However, it is particularly preferable when the distance between the wall of the downcomer in the region of the outflow orifice and the wall of the collecting cup in the region of the overflow is greater than the distance from the wall of the collecting cup outside the overflow. This can be achieved, for example, in the case of a square downcomer, by virtue of the collecting cup having a rectangular cross-sectional shape or, in the case of a circular downcomer, by an oval collecting cup. Alternatively, irrespective of the cross-sectional shape of the downcomer, it would be possible to provide a circular collecting cup, in which case the latter is arranged eccentrically with respect to the center of the downcomer. In principle, both the downcomer and the collecting cup could each independently have any desired cross-sectional shape, with the collecting cup disposed in relation to the downcomer in each case such that the distance between the wall of the downcomer and the overflow is greater than the distance between the wall of the downcomer and the wall of the collecting cup outside the overflow.

In order to minimize the influence of the downcomer on the gas flow, it is preferable when the downcomer has a cross-sectional constriction, such that the horizontal cross-sectional area of the downcomer at the inlet is greater than the horizontal cross-sectional area at the outlet. The reduction in the cross-sectional area of the downcomer makes it possible to configure the collecting cup in such a way that it has a cross-sectional area no greater than the cross-sectional area of the downcomer above the cross-sectional constriction. This too has the advantage that the regions which are not wetted by spraying liquid are minimized, such that the formation of deposits resulting from precipitated polymer is minimized.

The ratio of the horizontal cross-sectional area at the inlet to the horizontal cross-sectional area at the outlet of the downcomer is preferably in the range from 1:1 to 4:1, more preferably in the range from 1.5:1 to 3:1 and especially in the range from 1.8:1 to 2.5:1. In order to achieve the cross-sectional constriction, it is possible to configure the downcomer in the form of a funnel, such that all the walls that form the downcomer are inclined toward the middle of the downcomer. Alternatively, especially in the case of a downcomer having a non-circular cross section, it is also possible to provide only one wall or preferably two opposite walls having an inclination in the direction of the middle of the downcomer, such that the length of the downcomer parallel to the walls having inclination does not change, and only at right angles to the alignment of the walls having inclination does the width of the downcomer decrease.

According to the invention, the minimum horizontal cross-sectional area of the collecting cup is 1.2 to 4 times greater than the horizontal cross-sectional area of the downcomer at the outlet, preferably 1.5 to 3 times greater and especially 1.8 to 2.5 times greater. It is additionally preferable when the horizontal cross-sectional area of the collecting cup is 0.5 to 2 times as high as the horizontal cross-sectional area of the downcomer at the inlet, preferably 0.7 to 1.5 times as high and especially 0.8 to 1.2 times as high.

Irrespective of the nature of the cross-sectional constriction of the downcomer, it is preferable when the downcomer has an upper region having a constant cross section, a middle region in which the cross-sectional area decreases and a lower region which again has a constant cross section. The cross-sectional area of the upper region having constant cross section corresponds to the area of the inlet of the downcomer, and the cross-sectional area of the lower region to the cross-sectional area at the outlet. More preferably, the walls run vertically in the upper region and in the lower region.

As well as a configuration having three regions, however, it is also possible to provide only two regions, in which case the upper region has a constant cross-sectional area and the lower region a cross-sectional constriction, or the upper region the cross-sectional constriction and the lower region a constant cross-sectional area. It is also possible to implement the cross-sectional constriction over the entire length of the downcomer, such that it has only the region having cross-sectional constriction.

In the case of a non-circular configuration of the downcomer, it is particularly preferable when the downcomer is formed symmetrically with respect to a plane of symmetry that runs vertically in the middle of the downcomer. If, in this case, the downcomer has a reduction in cross section from the inlet in the direction of the outlet, the latter is preferably implemented in such a way that the walls that run parallel to the plane of symmetry are inclined in the direction of the plane of symmetry. In this case, the walls preferably run vertically in the upper region of the downcomer, are inclined in the middle region and run vertically again in the lower region. As described above, however, it is also possible here to configure the walls in such a way that only the region above the cross-sectional constriction or only the region below the cross-sectional constriction has a constant cross-sectional area, or else the cross-sectional area decreases from the top downward over the entire downcomer. Irrespective of the configuration of the downcomer with or without sections having constant cross-sectional area, it is preferable when, in the case of a configuration symmetrical with respect to a plane of symmetry that runs vertically in the middle of the downcomer, the walls of the downcomer that run parallel to the plane of symmetry have a region in which the wall runs at an angle of inclination between 10 and 80° with respect to the vertical, in order to form the cross-sectional constriction. Preferably, the wall is inclined at an angle between 20 and 60° with respect to the vertical and especially in the range from 30 to 50°. Smaller inclinations deflect the gas flow to a lesser degree, and so the spray shadow is also reduced in this way.

The downcomers are preferably disposed on a crossflow tray in such a way that there is a sufficient distance at least between some of the downcomers and the mass transfer column that at least one passage orifice for the gas can be formed between the downcomer and the outer edge of the crossflow tray.

In a preferred embodiment, all the downcomers on a tray are positioned such that the distance between the wall of the downcomer that projects through the tray and the outer edge of the tray is at least sufficiently great at every point that at least one passage orifice can be formed in the tray. In this way, it is ensured that the ascending gas flows through the liquid between the downcomer and the wall of the column as well. This further intensifies contact between the liquid and the gas. Liquid is also entrained with the gas flow at this point through the passage orifice between the outer edge of the tray and the downcomer, such that the walls of the column are wetted with liquid in the region between the edge of the tray and the downcomer as well, and no polymer deposits form.

The total area of the cross-sectional areas of the feeds of all the downcomers of a crossflow tray is preferably in the range from 0.2% to 5%, more preferably in the range from 0.2% to 4% and especially in the range from 0.5% to 2%.

A suitable configuration and arrangement of the downcomers of a crossflow tray is described, for example, in WO-A 2013/139590.

A mass transfer column of the invention for performing a mass transfer operation comprises at least two of the above-described crossflow trays. The crossflow trays are arranged such that the liquid flows through the downcomers of the upper tray onto the tray, then flows over the tray and flows through the downcomers of the tray onto a tray beneath or, in the case of the lowermost tray of the mass transfer column, is collected in the bottom of the column. In order to assure gas exchange, the passage orifices for the gas are formed in each tray. The number of orifices in each tray and the total cross-sectional area of the orifices is chosen such that the pressure of the gas below each tray in the mass transfer column is sufficient to prevent liquid from being able to run off the tray through the passage orifices for the gas. It is preferable, however, to configure the passage orifices with an edge projecting upward and a hood above it as a bubble cap, which prevents liquid from being able to run off the tray through the passage orifices.

In order to maximize the residence time of the liquid on each tray and hence the contact between gas and liquid on each tray, it is preferable when all the downcomers of a crossflow tray are disposed in the same half of the tray and every two superposed crossflow trays are arranged such that the downcomers of the upper crossflow tray end above the half of the lower crossflow tray in which there are no downcomers. In this way, the liquid in one half runs off onto the crossflow tray and in the other half runs off from the crossflow tray after the liquid has flowed from one half into the other half on the crossflow tray.

In a preferred embodiment, the mass transfer column of the invention is used for thermal separation of a mixture comprising (meth)acrylic monomers, in which a liquid and a gas stream are passed in countercurrent through the mass transfer column and the (meth)acrylic monomers are present either in the gas stream or in the liquid.

(Meth)acrylic monomers in the context of the present invention mean acrylic monomers and/or methacrylic monomers.

Acrylic monomers mean acrolein, acrylic acid and/or esters of acrylic acid. Methacrylic monomers mean methacrolein, methacrylic acid and/or esters of methacrylic acid.

More particularly, the (meth)acrylic monomers in the context of present invention include hydroxyethyl acrylate, hydroxyethyl methacrylate, hydroxypropyl acrylate, hydroxypropyl methacrylate, glycidyl acrylate, glycidyl methacrylate, methyl acrylate, methyl methacrylate, n-butyl acrylate, isobutyl acrylate, isobutyl methacrylate, n-butyl methacrylate, tert-butyl acrylate, tert-butyl methacrylate, ethyl acrylate, ethyl methacrylate, 2-ethylhexyl acrylate, 2-ethylhexyl methacrylate, N,N-dimethylaminoethyl acrylate and N,N-dimethylaminoethyl methacrylate.

On the industrial scale, (meth)acrolein and (meth)acrylic acid are prepared predominantly by catalytic gas phase oxidation of suitable $C3/C_4$ precursor compounds (or of precursor compounds thereof). In the case of acrolein and acrylic acid, propene and propane are preferably used as such precursor compounds. In the case of methacrylic acid and of methacrolein, isobutene and isobutane are the preferred precursor compounds.

As well as propene, propane, isobutene and isobutane, suitable starting materials, however, are also other compounds comprising 3 or 4 carbon atoms, such as isobutanol, n-propanol or precursor compounds thereof, for example the methyl ether of isobutanol. Acrylic acid can also be obtained by catalytic gas phase oxidation of acrolein, methacrylic acid correspondingly by catalytic gas phase oxidation of methacrolein.

In the context of the preparation processes, product gas mixtures are obtained, from which it is necessary to separate the (meth)acrylic acid and the (meth)acrolein.

Esters of (meth)acrylic acid are obtainable, for example, by direct reaction of (meth)acrylic acid and/or (meth)acrolein with the appropriate alcohols. However, in this case too, product mixtures are obtained, from which the (meth)acrylic esters have to be separated.

Irrespective of the preparation process and the (meth)acrylic monomers prepared, the (meth)acrylic monomers are separated off in a mass transfer column, preferably by a thermal separation process. In the thermal separation process, a liquid stream and a gas stream are conducted in countercurrent through the mass transfer column, the gas coming into intensive contact with the liquid. For the intensive contact, the mass transfer column comprises a plurality of the crossflow trays of the invention, on which liquid is present, through which the ascending gas bubbles.

More preferably, the thermal separation process is a condensation when the (meth)acrylic monomers are present in the gas stream, and a rectification when the (meth)acrylic monomers are present in the liquid. In this way, the (meth)acrylic monomers are always drawn off as a liquid at the bottom of the mass transfer column.

Embodiments of the invention are shown in the figures and are elucidated in detail in the description which follows.

Figure 2:
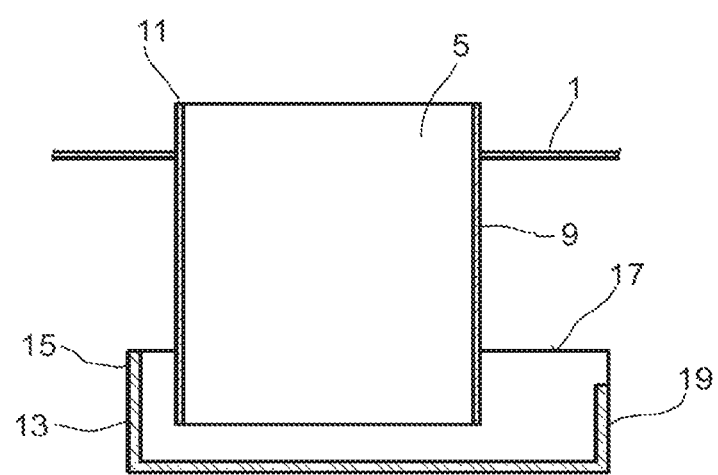
Figure 3:
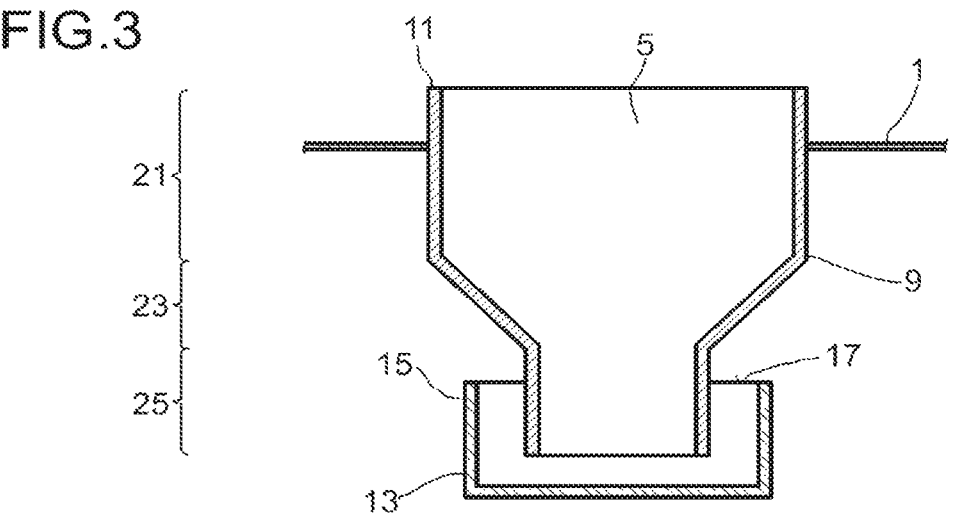
Figure 4:
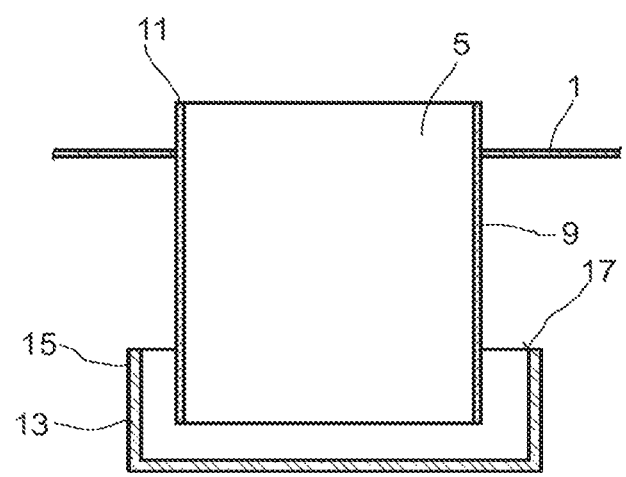
Figure 5:
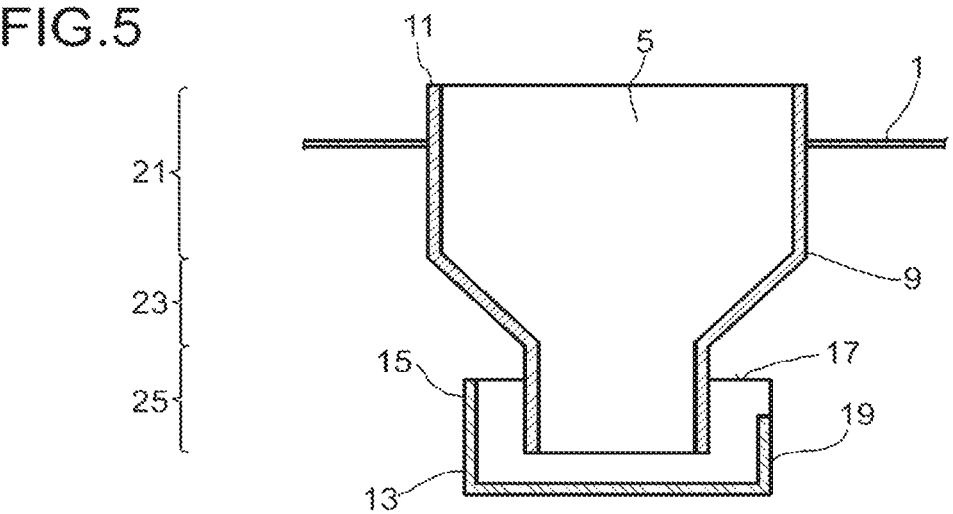
Figure 6:
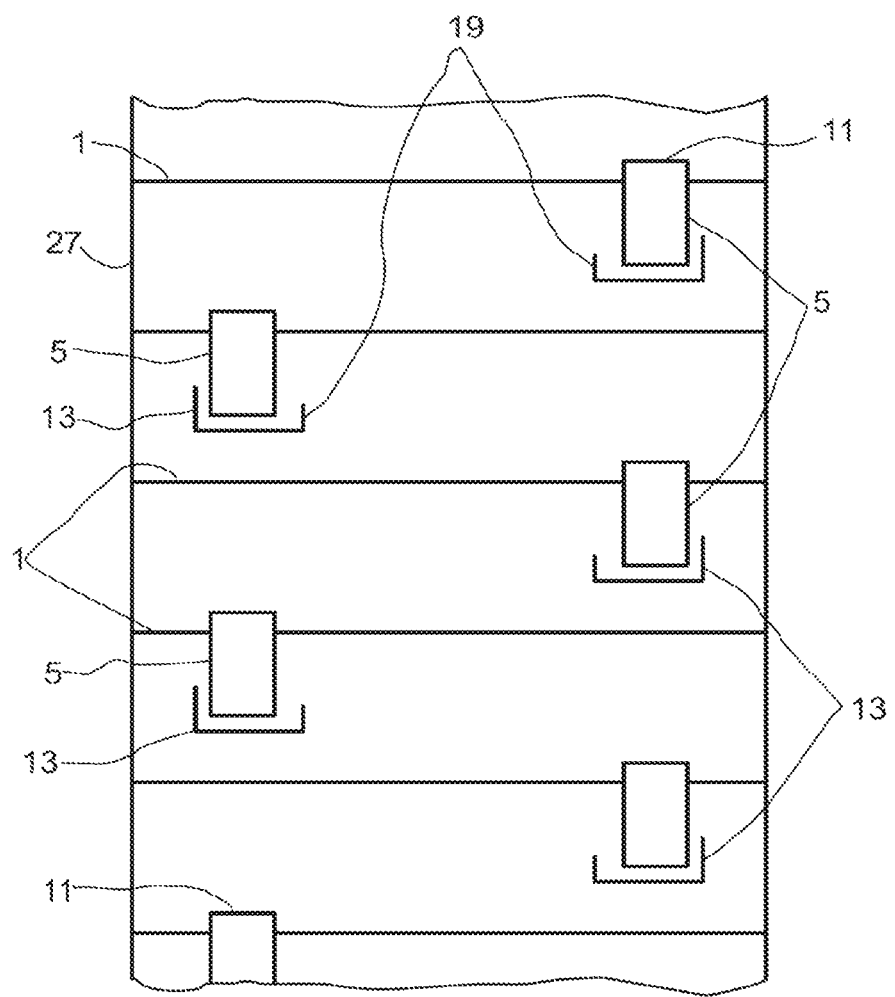

The figures show:

FIG. 1 a top view of a crossflow tray,

FIG. 2 a vertical section view through a downcomer in a first embodiment,

FIG. 3 a vertical section view through a downcomer in a second embodiment,

FIG. 4 a vertical section view through a downcomer in a third embodiment,

FIG. 5 a vertical section view through the downcomer according to FIG. 4 in a representation rotated by 90°, FIG. 6 a longitudinal section through a section of a mass transfer column.

FIG. 1 shows a top view of a crossflow tray.

A crossflow tray 1 which can be used in a mass transfer column has passage orifices 3 for a gas and downcomers 5 through which the liquid can run off from the crossflow tray 1.

In the operation of the mass transfer column, liquid passes through downcomers of an upper tray onto the crossflow tray 1. The liquid flows in the direction of the downcomers 5, with simultaneous flow of gas through the passage orifices 3. The passage orifices 3 for the gas preferably take the form of bubble caps having an edge pointing upward and a hood disposed above. As a result of this, the gas flows through the passage orifices, is deflected downward at the hood and is passed through the liquid surrounding the passage orifices. The hoods are configured in such a way that they project into the liquid. By virtue of the configuration of the passage orifices in the form of a bubble cap, no liquid can run off through the passage orifices 3. The liquid thus flows to the downcomers 5 and runs off through the downcomers 5 onto a tray beneath.

As an alternative to the configuration of the passage orifices 3 in the form of bubble caps, any other configuration known to those skilled in the art is also possible. The passage orifices 3 are configured in such a way that no liquid can run off through the passage orifices 3 in operation. When the passage orifices are configured in the form of holes as in the case of a sieve tray, the gas flow has to be adjusted in such a way that no liquid can run off through the passage orifices 3. Preference is given, however, to the configuration as a bubble cap, for example with a rectangular cross section as in the case of a Thormann® tray.

In order that the contact time between gas and liquid can be kept sufficiently high, the downcomers 5 of a tray are preferably, as shown in FIG. 1, all disposed in one half 7 of the crossflow tray 1. Within a mass transfer column, all the crossflow trays preferably have the same design, with every two immediately superposed trays rotated by 180° with respect to one another. As a result of this, the liquid on the upper tray flows onto the crossflow tray 1 in the half in which there are no downcomers. The liquid then runs into the other half 7 of the crossflow tray in which the downcomers 5 are disposed and runs off through the downcomers 5. In order to obtain a sufficiently high liquid level on the crossflow tray 1, the downcomers 5 preferably project beyond the surface of the crossflow tray 1 and form a weir over which the liquid flows into the downcomer 5.

The passage orifices 3 may, as shown here, take the form of rectangular slots. In this case, the long side of each slot is preferably aligned at right angles to the flow direction of the liquid. As well as the configuration of the passage orifices 3 in the form of rectangular slots, it is also possible to execute the passage orifices 3 in the form of elongated holes having rounded short sides, in oval form, in circular form, or with any desired cross-sectional shape. Preference is given, however, to a circular cross section or, as shown here, a rectangular cross section or the form of an elongated hole. The individual passage orifices 3 may, as shown here, be arranged in parallel rows. An alternative possibility, however, is a radial arrangement or an arrangement in which the passage orifices 3 of adjacent parallel rows are offset relative to one another. Also possible is any other arrangement of the passage orifices 3 with which sufficient contact of gas and liquid can be achieved and in which there is avoidance of liquid running off through the passage orifices 3.

As well as a configuration of the passage orifices as holes, it is also possible to configure the passage orifices in the form of valves or chimneys with a hood. In the case of a configuration as a chimney with a hood, the shape of the passage orifices corresponds to the shape as executed in tunnel-cap trays. In the case of circular passage orifices having a chimney and hood, the configuration corresponds to a bubble-cap tray.

When the passage orifices 3 are configured as valves, valve lids are present above the orifices and are raised by the gas flow, such that the gas can flow through the tray into the liquid that flows thereon. As soon as the gas flow is too weak or is interrupted, the orifices are closed by the valve lids, such that no liquid can run off from the tray through the orifices.

In principle, any configuration which is known to those skilled in the art and with which gas can be passed through a liquid flowing on the tray is possible.

According to the invention, the crossflow tray 1 has a plurality of downcomers 5. This achieves the effect that the liquid running off forms droplets and sprays over the entire region in which the downcomers 5 are disposed as a result of the liquid hitting the lower crossflow tray. Surprisingly, this leads to a reduction in polymer formation and in the formation of deposits.

Suitable configurations for the downcomers 5 are shown in FIGS. 2 and 3.

A downcomer 5 has a circumferential wall 9 which preferably, as shown here, projects upward beyond the crossflow tray 1. This forms a weir 11. The height of the weir 11 determines the height of the liquid on the crossflow tray 1. The higher the weir 11, the higher the liquid level has to be in order that liquid can flow from the crossflow tray 1 over the weir 11 into the downcomer 5.

Below the downcomer 5, according to the invention, there is a collecting cup 13. The collecting cups 13 has a circumferential wall 15 which is sufficiently high that the wall 9 of the downcomer 5 ends below the upper edge 17 of the circumferential wall 15 of the collecting cup 13. In operation, the effect of this is that liquid collects in the collecting cup 30 and the wall 9 of the downcomer 5 projects into the liquid. This creates a liquid seal, which prevents gas from being able to escape upward through the downcomer. All the gas thus has to flow through the passage orifices 3.

On one side of the circumferential wall 15 of the collecting cup 13, an overflow 19 is formed. The overflow 19, as shown in FIG. 2, can be implemented by virtue of the circumferential wall 15 having a lower height in the region of the overflow 19. Alternatively, it is also possible to configure the overflow, for example, in the form of orifices in the circumferential wall 15 of the collecting cup 13.

Irrespective of the form of the overflow, however, it should always be ensured that the edge that forms the overflow - here the upper end of the wall section that forms the overflow 19 - is above the lower end of the wall 9 of the downcomer 5, in order to assure the liquid seal. As described above, it is preferable when the overflow 19 is disposed on the side facing away from the shell of the mass transfer column.

As well as the embodiment of the downcomer 5 with a constant cross section, as shown in FIG. 2, it is also possible to configure the downcomer 5 with a cross-sectional constriction. It is thus either possible here to reduce the cross section over the entire length of the downcomer 5 or, as shown in FIG. 3, to configure the downcomer in an upper region 21 with a constant cross-sectional area, a middle region 23 with decreasing cross-sectional area and a lower region with constant cross-sectional area.

In the embodiment shown here, the wall of the downcomer 5 runs vertically in the upper region 21, such that the cross-sectional area remains constant. The upper region 21 is adjoined by the middle region 23, in which the walls are inclined such that the cross-sectional area of the downcomer 5 decreases from the top downward. In the lower region 25, the walls again run vertically downward, such that the cross-sectional area here is likewise constant.

It is particularly preferable when the downcomer 5 is formed symmetrically with respect to a plane of symmetry that runs vertically. In the case of a cross-sectional constriction, it is possible here that all the walls of the downcomer are inclined, such that the downcomer becomes smaller in terms of cross-sectional area in all directions from the top downward.

As an alternative, however, it is preferable when, in the case of a rectangular downcomer 5, two walls run vertically parallel over the entire length of the downcomer 5 and the two other opposite walls have an inclined section to form the cross-sectional reduction. In this case, the downcomer has a first cross section as shown in FIG. 2 and a second cross section rotated by 90° relative to the first cross section as shown in FIG. 3.

Irrespective of the configuration of the downcomer 5 with or without a cross-sectional constriction, the collecting cup 13, according to the invention, always has a region in which the overflow 19 is formed.

FIGS. 4 and 5 show a further embodiment of a downcomer. In this case, the section diagrams are rotated by 90° with respect to one another, and so FIG. 4 shows a section diagram at right angles to the center axis of the tray and FIG. 5 a section diagram parallel to the center axis of the tray.

In contrast to the embodiment shown in FIGS. 2 and 3, in the embodiment shown in FIGS. 4 and 5, the overflow 19 of the collecting cup 13 is arranged parallel to a wall having cross-sectional constriction. This has the advantage that the side of the collecting cup 13 that has the overflow 19 does not project beyond the cross-sectional area of the downcomer at the inlet. In this way, it is possible to reduce the spray shadow.

On the sides parallel to the sides without cross-sectional constriction, it is possible in this way to achieve a minimum protrusion of the collecting cup 13, as can be inferred from FIG. 5. The corresponding configuration of downcomer 9 and collecting cup 13 can achieve a minimum spray shadow.

When the downcomers are arranged as in FIG. 1, the overflows of all the collecting cups are preferably on the same side of the downcomers, and they especially point toward the diameter line aligned parallel to the long side of the passage orifices 3. When the downcomers have a circular cross section or are aligned in the radial direction, the middle of each overflow preferably points in the direction of the center of the crossflow tray 1. Alternatively, however, it is also possible in the case of circular downcomers that all the overflows 19 point in the same direction toward the outflow orifices of the lower tray.

FIG. 6 shows one possible arrangement of crossflow trays in a mass transfer column. For this purpose, only a section of the column is shown. The arrangement of the trays continues in the upward and downward directions. The top and bottom of the mass transfer column are configured here in the manner known to those skilled in the art. At the top of the column there is a gas outlet, and at the bottom of the column a liquid outlet. The feed into the column is dependent on the mass transfer process conducted. In the case of condensation, a gas is supplied in the lower region of the column, which ascends in the mass transfer column, with condensation of higher-boiling liquid on the individual trays. When the mass transfer process is a rectification, a liquid is added at the top and a heater is present at the bottom, such that the liquid boils on each tray, the gas ascends and non-boiling liquid runs off downward. In the case of a rectification, as well as an addition at the top, an addition of the liquid at the bottom or via a side feed is also possible.

In the case of a condensation too, the gas can be added via a side feed.

In order to obtain contact of maximum intensity between gas and liquid for each tray, the individual crossflow trays 1 in the mass transfer column 27 are each arranged with rotation of 180° with respect to one another. In this way, the downcomers 5 of successive trays are each on the opposite side in the mass transfer column 1, such that the liquid on each tray has to flow from the side of the downcomers 5 on the upper tray, through which the liquid arrives at the particular crossflow tray 1, to the downcomers 5 of the crossflow tray 1. Through passage orifices, which are not shown in FIG. 6, the gas flows from below through each crossflow tray, such that the gas flow prevents the liquid from being able to run off downward through the passage orifices. The liquid flows to the downcomer 5 and over the weir 11 into the downcomer 5, and is collected in the collecting cup 13. From the collecting cup 13, the liquid flows over the overflow 19 onto the crossflow tray 1 beneath. In this case, the overflows 19 are preferably each aligned in the direction of the downcomers 5 of the crossflow tray 1 beneath.

EXAMPLES

Comparative example

The procedure is in accordance with the example described in WO 2013/139590. It has been found here that no formation of unwanted polymer in the condensation column was detectable yet after 70 days of uninterrupted operation as described in WO 2013/139590, but such formation is found after 3 months, which necessitated cleaning of the column.

Example 1

In the process described in WO 2013/139590, the downcomers and collecting cups of the Thormann® trays of the condensation column were replaced by downcomers which had a rectangular cross-sectional shape and a cross-sectional constriction as shown in FIGS. 4 and 5, with twice as high a cross-sectional area at the inlet as the cross-sectional area at the outlet. The collecting cup likewise had a cross-sectional area which was twice as high as the cross-sectional area of the outlet. The collecting cups each had side walls projecting upward at right angles, and the side wall that pointed toward the center axis of the tray was lower and thus formed an overflow. The overflow was positioned below the area of the inlet and projected beyond the area of the downcomer only laterally on the non-constricted sides.

Each of the Thormann® trays was equipped with 8 downcomers, all of which had the same geometry and which were aligned parallel to one another.

The column was operated as in WO 2013/139590. It was found here that no deposits have formed yet even after six months.

LIST OF REFERENCE NUMERALS 1 crossflow tray
3 passage orifice
5 downcomer
7 half of the crossflow tray with downcomers 5
9 wall
11 weir
13 collecting cup
15 circumferential wall
17 upper edge
19 overflow
21 upper region
23 middle region
25 lower region

The invention claimed is:

1. A crossflow tray for a mass transfer column in which a gas is conducted in countercurrent to a liquid, the crossflow tray having passage orifices for the gas and at least two downcomers, the downcomers projecting beyond the top surface of the crossflow tray and a collecting cup being disposed beneath each downcomer wherein the downcomer projects into the collecting cup, the minimum horizontal cross-sectional area of the collecting cup being 1.2 to 4 times greater than the horizontal cross-sectional area of the downcomer at the outlet, and where the collecting cup has a circumferential wall having an overflow, the overflow being disposed only on the side of the collecting cup facing away from the shell of the mass transfer column.

2. The crossflow tray according to claim 1, wherein the circumferential wall of the collecting cup forms the overflow by having a lower height in the region of the overflow.

3. The crossflow tray according to claim 1, wherein the circumferential wall runs at right angles to the base of the collecting cup.

4. The crossflow tray according to claim 1, wherein the downcomer has a cross-sectional constriction, such that the horizontal cross-sectional area of the downcomer at the inlet is greater than the horizontal cross-sectional area at the outlet.

5. The crossflow tray according to claim 4, wherein a ratio of the horizontal cross-sectional area at the inlet to the horizontal cross-sectional area at the outlet is in the range from 1:1 to 4:1.

6. The crossflow tray according to claim 1, wherein the downcomer is formed symmetrically with respect to a plane of symmetry that runs vertically in the middle of the downcomer.

7. The crossflow tray according to claim 4, wherein the walls of the downcomer that run parallel to the plane of symmetry have a region in which the wall runs at an angle of inclination between 10 and 80° with respect to the vertical, in order to form the cross-sectional constriction.

8. The crossflow tray according to claim 7, wherein the wall of the downcomer runs vertically above and below the region inclined with respect to the vertical.

9. The crossflow tray according to claim 1, wherein all the downcomers are positioned such that the distance between the wall of the downcomer that projects through the crossflow tray and the outer edge of the crossflow tray is at least sufficiently great at every point that at least one passage orifice can be formed in the crossflow tray.

10. A mass transfer column for conducting a mass transfer operation, comprising at least two crossflow trays according to claim 1.

11. The mass transfer column according to claim 10, wherein all the downcomers of a crossflow tray are disposed in the same half of the crossflow tray and every two superposed crossflow trays are arranged such that the downcomers of the upper crossflow tray end above the half of the lower crossflow tray in which there are no downcomers.

12. A method for thermal separation of a mixture comprising (meth)acrylic monomers conducted in the mass transfer column according to claim 10, comprising:
    passing a liquid and a gas stream in countercurrent through the mass transfer column wherein the (meth)acrylic monomers are present either in the gas stream or in the liquid.

13. The method according to claim 12, wherein the thermal separation process is a condensation when the (meth)acrylic monomers are present in the gas stream and a rectification when the (meth)acrylic monomers are present in the liquid.

* * * * *

UNITED STATES PATENT AND TRADEMARK OFFICE
CERTIFICATE OF CORRECTION

PATENT NO. : 10,183,234 B2  
APPLICATION NO. : 15/072463  
DATED : January 22, 2019  
INVENTOR(S) : Tim Blaschke et al.

Page 1 of 1

It is certified that error appears in the above-identified patent and that said Letters Patent is hereby corrected as shown below:

In the Claims

In Column 12, Line 65, Claim 1, delete "downcomer" and insert -- downcomer, --, therefor.

Signed and Sealed this
Twenty-sixth Day of November, 2019

Andrei Iancu
*Director of the United States Patent and Trademark Office*